United States Patent
Hansen et al.

[11] Patent Number: 6,142,775
[45] Date of Patent: Nov. 7, 2000

[54] OCCLUSAL CAP FOR ORTHODONTIC BRACKET

[75] Inventors: James D. Hansen, Pasadena; James D. Cleary, Glendora; Jirina V. Pospisil, Covina, all of Calif.

[73] Assignee: 3M Innovative Properties Company, St. Paul, Minn.

[21] Appl. No.: 09/353,699

[22] Filed: Jul. 14, 1999

[51] Int. Cl.[7] .................................................. A61C 3/00
[52] U.S. Cl. .................................................. 433/8; 433/14
[58] Field of Search .................................. 433/8, 10, 11, 433/13, 14, 17, 22

[56] References Cited

U.S. PATENT DOCUMENTS

| | | | |
|---|---|---|---|
| 3,772,787 | 11/1973 | Hanson | 32/14 |
| 3,838,514 | 10/1974 | Polak | 433/8 |
| 4,103,423 | 8/1978 | Kessel | 32/14 |
| 4,248,588 | 2/1981 | Hanson | 433/11 |
| 4,302,532 | 11/1981 | Wallshein | 433/8 |
| 4,355,975 | 10/1982 | Fujita | 433/13 |
| 4,492,573 | 1/1985 | Hanson | 433/11 |
| 4,527,975 | 7/1985 | Ghafari et al. | 433/8 |
| 4,559,012 | 12/1985 | Pletcher | 433/10 |
| 4,712,999 | 12/1987 | Rosenberg | 433/8 |
| 4,950,158 | 8/1990 | Barngrover et al. | 433/11 |
| 5,160,260 | 11/1992 | Chang | 433/22 |
| 5,203,804 | 4/1993 | Nikutowski et al. | 433/8 |
| 5,288,230 | 2/1994 | Nikutowski et al. | 433/20 |
| 5,317,074 | 5/1994 | Hammar et al. | 528/44 |
| 5,358,402 | 10/1994 | Reed et al. | 433/8 |
| 5,366,372 | 11/1994 | Hansen et al. | 433/4 |
| 5,380,196 | 1/1995 | Kelly et al. | 433/8 |
| 5,439,379 | 8/1995 | Hansen | 433/8 |
| 5,454,716 | 10/1995 | Banerjee et al. | 433/20 |
| 5,461,133 | 10/1995 | Hammar et al. | 528/10 |
| 5,516,284 | 5/1996 | Wildman | 433/10 |
| 5,575,645 | 11/1996 | Jacobs et al. | 433/9 |
| 5,630,715 | 5/1997 | Voudouris | 433/13 |
| 5,685,711 | 11/1997 | Hanson | 433/11 |
| 5,738,513 | 4/1998 | Hermann | 433/13 |
| 5,762,192 | 6/1998 | Jacobs et al. | 206/369 |
| 5,857,849 | 1/1999 | Kurz | 433/10 |
| 5,857,850 | 1/1999 | Voudouris | 433/11 |
| 5,993,207 | 11/1999 | Spencer . | |

FOREIGN PATENT DOCUMENTS

| | | | |
|---|---|---|---|
| WO97/29712 | 8/1997 | WIPO | A61C 7/12 |
| WO98/20805 | 5/1998 | WIPO | A61C 7/28 |

*Primary Examiner*—Todd E. Manahan
*Attorney, Agent, or Firm*—James D. Christoff

[57] ABSTRACT

A cap is releasably connected to an orthodontic bracket and covers tips of occlusal bracket tiewings in order to prevent contact of the bracket with the enamel of opposing dentition. The cap includes a section that extends at least partially along a channel of the bracket extending in a generally occlusal-gingival direction in order to help retain the cap in its intended position and prevent the cap from rotating relative to the bracket. In preferred embodiments, the cap is made of a stain-resistant aesthetically pleasing material. Optionally, the cap serves as a ligature in order to retain an archwire in an archwire slot of the bracket.

43 Claims, 7 Drawing Sheets

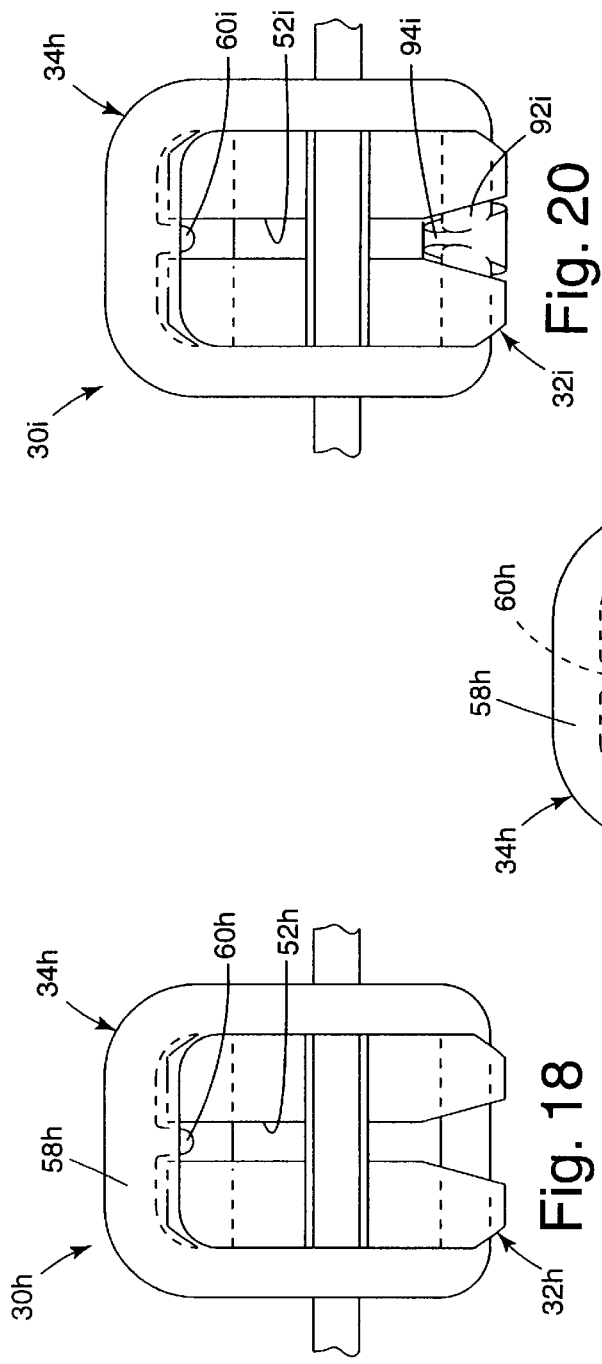

OCCLUSAL CAP FOR ORTHODONTIC BRACKET

BACKGROUND OF THE INVENTION

I. Field of the Invention

This invention relates to an attachment for an orthodontic bracket. More particularly, the present invention is directed toward a cap for covering the occlusal tip of one or more occlusal tiewings of an orthodontic bracket.

II. Description of the Related Art

Orthodontic treatment involves movement of malpositioned teeth to orthodontically correct locations for an improved appearance and/or improved occlusion. During one type of orthodontic treatment program, tiny appliances known as brackets are fixed to the buccolabial surfaces of the teeth (i.e., the surfaces facing the cheeks or lips), and an archwire is placed in a slot of each bracket. The archwire forms a track to guide movement of the teeth to desired locations.

Oftentimes, the patients' upper dental arch and the patient's lower dental arch receive a set of brackets and an archwire. Ends of the archwires are typically placed in buccal tubes that are fixed to the patient's molar teeth. The orthodontist may place bends or twists in the archwire to facilitate movement of the teeth, or couple elastic members or other force generating modules to the brackets in order to urge the associated teeth to desired positions.

While orthodontic brackets have decreased in size over the years, the brackets still protrude outwardly some distance away from the underlying tooth surfaces in a buccolabial direction. In many instances, the protrusion of the brackets does not present any significant problems. However, in some instances, the brackets mounted on the patient's lower dental arch can come into contact with teeth of the upper dental arch when the patient's jaws are closed. Contact of the brackets with opposing dentition frequently occurs in patients having a deep bite, a condition where the upper incisor teeth overlap the lower incisor teeth an excessive distance when the patient's jaws are closed.

When orthodontic brackets contact the patient's opposing dentition, the brackets can wear down the outer enamel layer of the teeth to such an extent that a significant amount of enamel is removed. This problem is particularly acute when the brackets are made of ceramic material. The ceramic material may be aesthetically pleasing when mounted on the patient's teeth during an orthodontic treatment program, but the ceramic material is substantially harder than the relatively soft tooth enamel and can abrade the enamel to a significant extent in a relatively short amount of time in certain instances.

Orthodontic brackets are also commonly made of metallic materials and plastic materials. While the hardness of metal brackets is less than the hardness of ceramic brackets, the repeated contact of metal brackets against the tooth enamel can also cause wear on the teeth to some extent. On the other hand, plastic brackets are typically much softer than the tooth enamel, but in some instances the teeth may wear away portions of the plastic brackets to such a degree that they do not function as intended.

In the past, a number of methods have been proposed for preventing undue wear of the patient's teeth caused by brackets mounted on opposing dentition. One method involves mounting a set of brackets initially only on the patient's upper dental arch in order to open the patient's bite before the brackets are mounted on the patient's lower arch. Unfortunately, treatment of the patient's lower dental arch is delayed to some extent by following this method, with the result that the overall length of treatment time is increased.

Another method for attempting to avoid or reduce contact of orthodontic brackets with opposing dentition involves the use of a device known as a bite plate that is bonded to the lingual side (i.e., the side facing the patient's tongue) of the upper anterior teeth. The bite plate prevents the patient from completely closing his or her jaws, so that the teeth of the patient's upper dental arch cannot contact the teeth of the lower dental arch. Unfortunately, the use of bite plates is not considered satisfactory by many practitioners, due in part to the expense of the device and also due to the amount of time needed for preparation of the patient's teeth and careful positioning of the devices on the teeth.

U.S. Pat. No. 4,950,158 describes an elastomeric device that functions as a ligature for orthodontic brackets and also serves to reduce wear of the teeth on the opposing dental arch. The device is made of an elastomeric material and presents an enlarged, protruding bumper portion that extends across an occlusal side of the associated bracket (i.e., along a side facing the outermost or occlusal tips of the patient's teeth). The device has a generally annular shape and is received behind tiewings of the bracket as well as over the archwire in order to urge the archwire toward a fully seated position in the archwire slot.

In addition to the devices described in U.S. Pat. No. 4,950,158, practitioners have also attempted to use orthodontic rotation wedges to prevent wear on opposing dentition. However, such devices are not entirely satisfactory in that they may rotate to a position wherein the enlarged bumper portion or the enlarged wedge portion is no longer located along an occlusal side of the associated bracket. This problem is more likely to occur after the devices have been in use for such a period of time that the elastic material has relaxed and no longer tightly grips the associated bracket.

SUMMARY OF THE INVENTION

The present invention overcomes the disadvantages noted above by provision of an occlusal cap that is releasably received on an orthodontic bracket. The cap includes at least one section that is positioned to substantially prevent rotation of the cap in use. As a result, the cap remains in place across the occlusal side of the associated bracket and serves to substantially prevent direct contact of the bracket with the enamel of opposing teeth.

In more detail, the present invention in one embodiment concerns an orthodontic bracket assembly that comprises an orthodontic bracket and a cap. The orthodontic bracket has a mesial-occlusal tiewing, a distal-occlusal tiewing, a mesial-gingival tiewing and a distal-gingival tiewing. The bracket includes an archwire slot extending in a generally mesial-distal direction between the mesial-occlusal tiewing and the mesial-gingival tiewing and between the distal-occlusal tiewing and the distal-gingival tiewing. The mesial-occlusal tiewing and the distal-occlusal tiewing each have an outermost, occlusal tip. The bracket also has a channel extending in a generally occlusal-gingival direction between at least part of the mesial-occlusal tiewing and the distal-occlusal tiewing. The cap is releasably connected to the bracket and includes a first section extending over the occlusal tiewing tips in occlusal relation thereto. The cap also includes a second section extending at least partially along the channel.

Another embodiment of the present invention is directed toward an orthodontic bracket assembly that comprises an orthodontic bracket and a cap. The orthodontic bracket has a mesial-occlusal tiewing, a distal-occlusal tiewing and at least one gingival tiewing. The mesial-occlusal tiewing and the distal-occlusal tiewing each include an outermost occlusal tip. The bracket includes an archwire slot extending in a generally mesial-distal direction. The bracket also has a channel extending in a generally occlusal-gingival direction between at least part of the mesial-occlusal tiewing and the distal-occlusal tiewing. The cap is releasably connected to the bracket and includes a first section extending over the occlusal tips in occlusal relation thereto. The cap also has a second section that extends at least partially along the channel.

The present invention is also directed in another embodiment to an occlusal cap for an orthodontic bracket. The cap has a first section and a second section. The first section includes at least one concave portion for covering at least one occlusal tiewing tip of the bracket. The second section extends outwardly from the first section for reception in a channel of the bracket that extends in a generally occlusal-gingival direction.

The second section of the cap as described above in the various embodiments serves to prevent rotation of the cap relative to the associated bracket in use. As such, the cap remains positioned to act as a barrier or shield and substantially prevent contact of the associated bracket with the enamel of opposing teeth. Once the teeth have been moved to such an extent that the cap is no longer needed, the cap can be readily removed from the bracket if desired.

Optionally, the first section of the cap is made of an aesthetically pleasing material that tends to blend in with the adjacent teeth. For example, the first section may be made of a stain-resistant polymeric material that is translucent or that has the color of natural teeth. Optionally, the cap may include structure for ligating an archwire to the archwire slot of the associated bracket if desired.

These and other aspects of the invention are described in more detail in the paragraphs that follow and are illustrated in the accompanying drawings.

BRIEF DESCRIPTION OF THE DRAWINGS

FIG. 18 is a front elevational view looking in a lingual direction of an orthodontic bracket and cap assembly according to a further embodiment of the invention;

FIG. 19 is a front elevational view looking in a lingual direction of the cap alone that is shown in FIG. 18, and showing the cap as it appears in its relaxed state before assembly to the bracket;

FIG. 20 is a front elevational view looking in a lingual direction of an orthodontic bracket and cap assembly according to yet another embodiment of the invention;

FIG. 21 is a front elevational view looking in a lingual direction of the cap alone that is shown in FIG. 20, and illustrating the cap as it appears in its relaxed state before assembly to the bracket; and FIG. 22 is a side cross-sectional view of the cap shown in FIG. 21 and taken along lines 22—22 of FIG. 21.

DETAILED DESCRIPTION OF THE PREFERRED EMBODIMENTS

Figure 1:
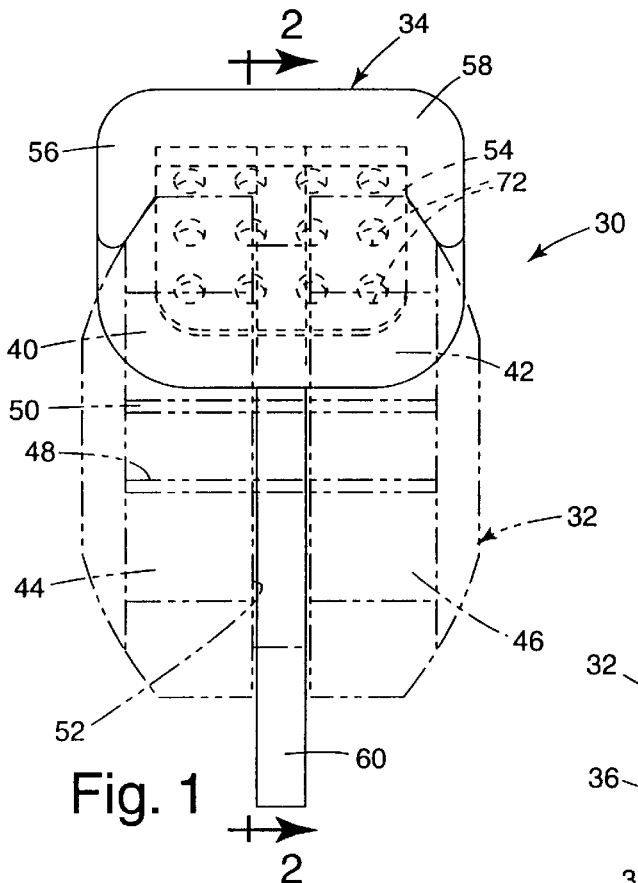
FIG. 1 is a front elevational view looking in a lingual direction of an orthodontic bracket and cap assembly according to one embodiment of the present invention.
Figure 2:
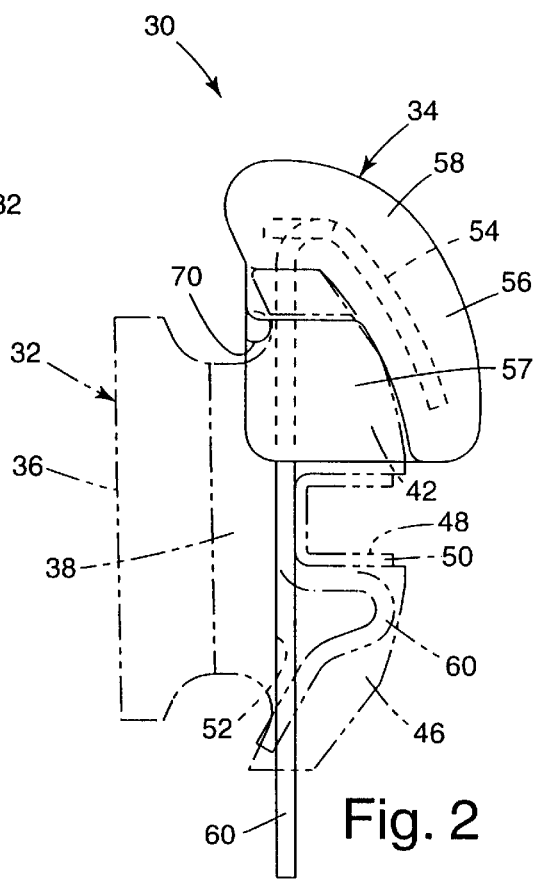
FIG. 2 is a side cross-sectional view of the assembly illustrated in FIG. 1 and taken along lines 2—2 of FIG. 1.

An orthodontic bracket assembly according to one embodiment of the present invention is designated broadly by the numeral 30 in FIGS. 1 and 2. The assembly 30 includes an orthodontic bracket 32 as well as an orthodontic cap 34 that is releasably connected to the bracket 32. The cap 34 is shown alone in FIGS. 3 and 4.

The bracket 32 includes a tooth-facing base 36 and a body 38 that extends outwardly from the base 36 in a buccolabial direction. The base 36 in this embodiment is adapted to be directly bonded to a labial surface of the tooth by an adhesive, and has a compound, concave contour that matches the convex configuration of the labial surface of the tooth. Optionally, the base 36 has a structure such as grooves, particles, spheres, a layer of a chemical bonding agent or the like or any combination thereof in order to enhance the strength of the bond between the bracket 32 and the underlying tooth.

As another option, the base 36 may not be directly bonded to the tooth, and instead be fixed by welding or brazing to an orthodontic band. The band is shaped to encircle the patient's tooth and may be preferable in some instances to directly-bonded brackets. The band is not shown in the drawings, but could be similar to any conventional band known in the art.

The bracket 32 also includes a mesial-occlusal tiewing 40, a distal-occlusal tiewing 42, a mesial-gingival tiewing 44 and a distal-gingival tiewing 46. The tiewings 40, 42, 44 and 46 are integrally connected to the body 38. The tiewings 40, 42 extend in an occlusal direction (i.e., in a direction toward to outer tips of the patient's teeth) and the tiewings 44, 46 extend in a gingival direction (i.e., in a direction toward the patient's gingiva or gums). A notch or undercut is located on a lingual side of each of the tiewings 40, 42, 44, 46 for receiving a ligature in order to connect an archwire (not shown) to the bracket 32.

An archwire slot 48 extends in a generally mesial-distal direction (i.e., in a direction along a line extending from the center of the patient's dental arch and to either end of the patient's dental arch). In the embodiment shown in the drawings, the archwire slot 48 is surrounded on three sides by an archwire slot liner 50 that is secured to the body 38 and tiewings 40, 42, 44, 46. Once the archwire is inserted in the archwire slot 48 and held in place by a ligature as mentioned above, the archwire serves as a track to guide movement of the bracket 32 and hence movement of the underlying tooth to a position as determined by the practitioner.

The bracket 32 may be made of any suitable material known in the art, including monocrystalline or polycrystalline ceramic, metallic materials (such as 17-4 stainless steel, or 303 or other Series 300 stainless steel) and plastic materials (such as polycarbonate and polycarbonate reinforced with glass fibers). The bracket 32 that is shown in the drawings may be similar or identical to the brackets described in U.S. Pat. Nos. 5,439,379 and 5,366,372, both of which are incorporated by reference herein. The archwire slot liner 50 may be brazed to ceramic material by the methods described in U.S. Pat. Nos. 5,358,402 and 5,380,196, which are also incorporated by reference herein.

The bracket 32 also includes a channel 52 that extends in a generally occlusal-gingival direction between the tiewings 40, 42, and between the tiewings 44, 46. The channel 52 is sometimes called a "vertical" channel, but may not extend in a true vertical direction. Optionally, and as shown in the illustrated embodiment, the channel 52 extends on a lingual side of the archwire slot liner 50. Optionally, the channel 52 is a slot that serves to completely separate the tiewings 40, 42 and also completely separate the tiewings 44, 46. As an alternative, however, the channel 52 is a notch that only partially separates the tiewings.

The cap 34 includes a framework 54 as well as a covering 56 that extends over an occlusal portion of framework 54. The majority of the covering 56 along with underlying portions of the framework 54 represent a first section 58 of the cap 34. The cap 34 also includes a second section 60 which is represented by remaining portions of the framework 54 as well as a leg 57 of the covering 56.

Figure 3:
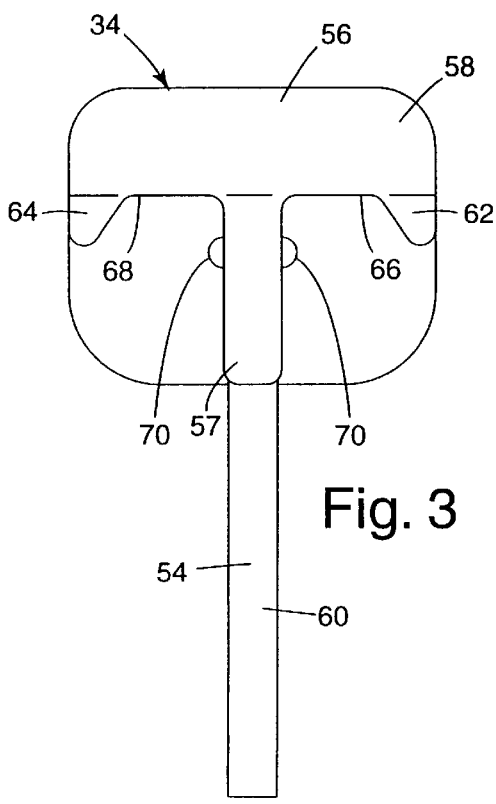
FIG. 3 is a rear elevational view looking in a buccolabial direction toward the cap alone of the assembly of FIGS. 1 and 2.
Figure 4:
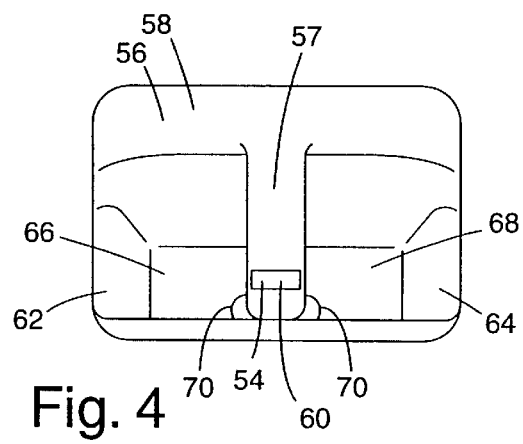
FIG. 4 is an end elevational view looking in an occlusal direction of the cap alone as shown in FIG. 3.

The first section 58 of the cap 34 extends over the occlusal tips of the mesial-occlusal tiewing 40 and the distal-occlusal tiewing 42. More particularly, the first section 58 preferably extends over the occlusal ends of the tiewings 40, 42 as well as across at least a portion of the labial surfaces of the tiewings 40, 42. As shown in FIGS. 3 and 4, the first section 58 also includes a mesial portion 62 that extends partially along the mesial side of the mesial-occlusal tiewing 40, and a distal portion 64 that extends partially along a distal side of the distal-occlusal tiewing 42. The first section 58 preferably includes two concave portions 66, 68 for receiving the outer occlusal tips of the tiewings 40, 42 respectively. Preferably, the concave portions 66, 68 are complimental in configuration to the outer tips of the tiewings 40, 42 for snug reception of the latter.

The second section 60 extends in a generally occlusal-gingival direction away from the first section 58 and is detachably received in the channel 52. The metal framework portion of the second section 60 is initially elongated and straight as shown in FIG. 3. However, once the cap 34 has been assembled to the bracket 32 and the second section 60 (including the leg 57) is received in the channel 52, the metal framework portion of the second section 60 may be deformed past its yield point by pushing its outer end in an occlusal direction until the second section 60 assumes the bent configuration shown in dashed lines in FIG. 2. Optionally, the deformation may be carried out by first lifting the outer, gingival end of the second section 60 with a dental scaler or pliers and then pushing the second section 60 toward the illustrated configuration.

Once bent, the second section 60 retains the cap 34 in assembled relation to the bracket 32. The cap 34 can be detached from the bracket 32 when desired by straightening the second section 60 and then moving the cap 34 in occlusal direction until the second section 60 is free from the channel 52. The second section 60 may be straightened by first lifting its outer end out of the channel 52, and then bending the second section 60 to a straight configuration.

Preferably, the cap 34 includes a pair of protrusions 70 that snap in place along a lingual side of the tiewings 40, 42 respectively when the cap 34 is assembled to the bracket 32. The protrusions 70 serve to help retain the cap 34 in assembled relationship to the bracket 32 so that the cap 34 does not shift or become unintentionally dislodged during the course of treatment.

The covering 56 is preferably made from a stain resistant polymer having a hardness that is less or equal to the hardness of tooth enamel. Suitable stain resistant polymers include fluoropolymers such as described in applicant's co-pending U.S. patent application Ser. No. 09/262,628, which is incorporated by reference herein. Other suitable stain resistant polymers are described in applicant's U.S. Pat. Nos. 5,317,074 and 5,461,133.

Optionally, the covering 56 may be transparent or translucent, or alternatively may be opaque. If the covering 56 is opaque, the covering 56 preferably has a color that matches or blends in with the color of adjacent teeth, such as off-white shades and the various tooth-colored shades of the Vita scale. As another option, the covering 56 may have a color that matches or blends in with the color of the bracket 32.

As shown in dashed lines in FIG. 1, a portion of the framework 54 that is embedded in the covering 56 preferably includes a series of apertures 72. The apertures receive a portion of the covering 56 when the latter is molded to the framework 54, and provide mechanical retention to hinder separation of the covering 56 from the framework 54 once the polymeric material of the covering 56 has cured.

The framework 54 is preferably made of a metallic material that is strong yet can be bent when desired by the practitioner to the curved configuration shown in the dashed lines in FIG. 2 in order to retain the cap 34 in assembled relationship to the bracket 32. If the covering 56 is transparent or translucent, the metallic material is preferably covered with an aesthetic coating that matches or blends in with the color of the adjacent teeth. Examples of suitable colors for the coating include off-white shades and the various tooth-colored shades of the Vita scale.

Suitable compositions for the coating of the framework 54 include paints, inks and the like. For example, the coating may be made of a resin binder and an opacifying filler. Suitable resins include acrylics, methacrylics, epoxies, liquid crystal polymers, acetals, nylons, polyurethanes, polysulfones, polyamids, polyimids, polyacetates, phenolics, polyesters and amino type resins such as melamine formaldehyde and urea formaldehyde, and combinations thereof.

Suitable fillers for the coating include aluminum oxide, zirconium oxide, titanium dioxide, silicone dioxide and boron nitride. The size of the filler particles should be very small since the coating may be quite thin.

Other suitable compositions for the coating are described in U.S. Pat. No. 5,454,716 and in PCT Published Appln. No. WO97/29712, both of which are incorporated by reference. The coating may also include a fluoride releasing compound such as sodium fluoride, potassium fluoride, zinc fluoride or fluoraluminosilicates.

Preferably, the coating is highly resistant to staining by food and beverages so that the coating does not significantly discolor when used over a period of time in the oral cavity. For example, the coating should be resistant to staining by mustard, catsup, cranberry juice, tea, curry powder, blueberries, coffee and the like. Suitable coatings do not show any significant staining after immersion of the cap 34 in such materials for 24 hours.

The coating may be applied to the framework 54 by various techniques including spraying, wiping, electrostatic coating, electrolytic coating, electrophoretic coating, vacuum surface coating and/or any of the various processes described in the aforementioned U.S. Pat. No. 5,454,716 and PCT Published Appln. No. WO97/29712. The coating may be applied as a single layer or in a plurality of layers, and is optionally fully or partially cured between applications of successive layers. Preferably, at least the topcoat layer is significantly resistant to staining by food and beverages as described above.

As other options, the coating may be a hard carbon coating or may comprise one or more coating compositions described earlier in combination with a topcoat made of a hard carbon coating. Suitable hard carbon coatings and application techniques are described, for example, in U.S. Pat. Nos. 5,203,804 and 5,288,230, both of which are incorporated by reference herein.

In use, the cap 34 serves to protect the tooth enamel of opposing dentition from contact with the bracket 32, and particularly from contact with the tiewings 40, 42 of the bracket 32. Since the covering 56 is made of a material that is softer than the tooth enamel, the tooth enamel does not wear or abrade to any significant extent when contacting the cap 34, such as when the patient's jaws are repeatedly closed.

If the bracket 32 is made of a relatively hard material such as ceramic, the covering 56 is preferably made of a material that is softer and more resilient than the material of the bracket 32. In that instance, the framework 54 is also preferably softer than the material of the bracket 32 and consequently provides some degree of protection against wear of the patient's enamel of opposing teeth if the covering 56 is accidentally detached from the framework 54 or wears away after an extended period of time. Alternatively, if the bracket 32 is made of a relatively soft material such as a polymeric material, the covering 56 is preferably made of a material that is harder and stiffer than the material of the bracket 32 in order to prevent undue wear on the bracket 32 (such as the tiewings 40,42) during the course of treatment.

The second section 60 is a significant advantage, in that the reception of the second section 60 in the channel 52 hinders movement of the cap 34 relative to the bracket 32 and serves to retain the cap 34 in place. Additionally, provision of the second section 60 in combination with the channel 52 enables the cap 34 to be readily installed on the bracket 32 when desired, or easily detached from the bracket 32 when no longer needed. The concave portions 66, 68, the mesial and distal portions 62, 64 and the protrusions 70 also help to immobilize the cap 34 relative to the bracket 32 when assembled together.

When the bracket 32 is made of a metallic material such as stainless steel, the cap 34 can provide an aesthetic cover that partially hides the bracket 32. For example, when the covering 56 is made of an aesthetic material as described above, the covering 56 blends in with the color of the adjacent teeth and underlying portions of the bracket 32 are obscured.

The framework 54 also provides reinforcement for the cap 34, a particular advantage when the covering 56 is made of certain polymeric materials. For example, when the covering 56 is made of a polymeric material that is relatively soft, the framework 54 provides sufficient strength and rigidity to hold the covering 56 in place during the expected course of treatment.

Figure 5:
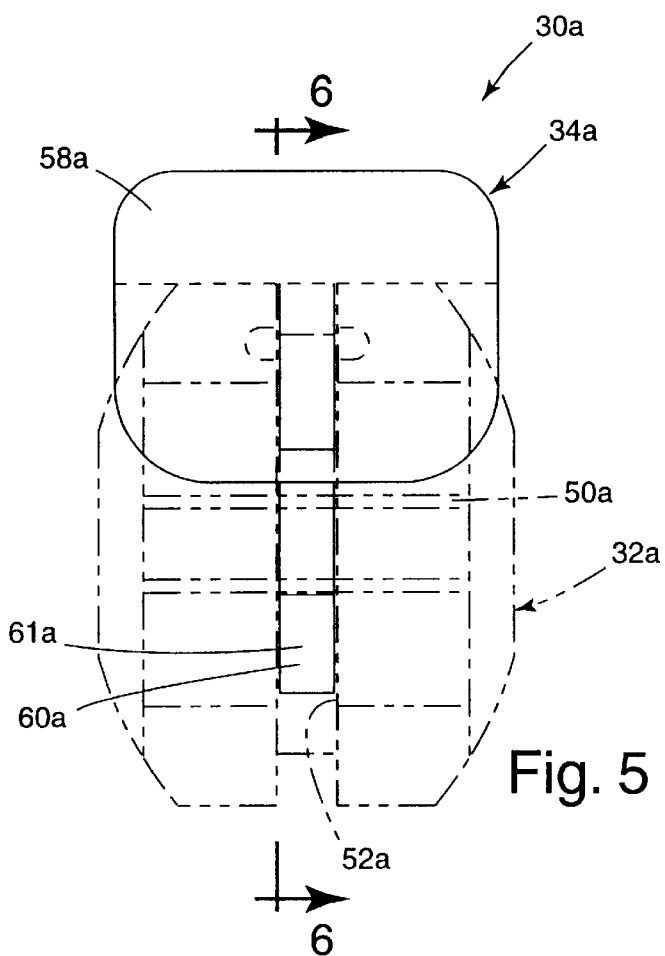
FIG. 5 is a front elevational view looking in a lingual direction of an orthodontic bracket and cap assembly constructed according to another embodiment of the invention.
Figure 6:
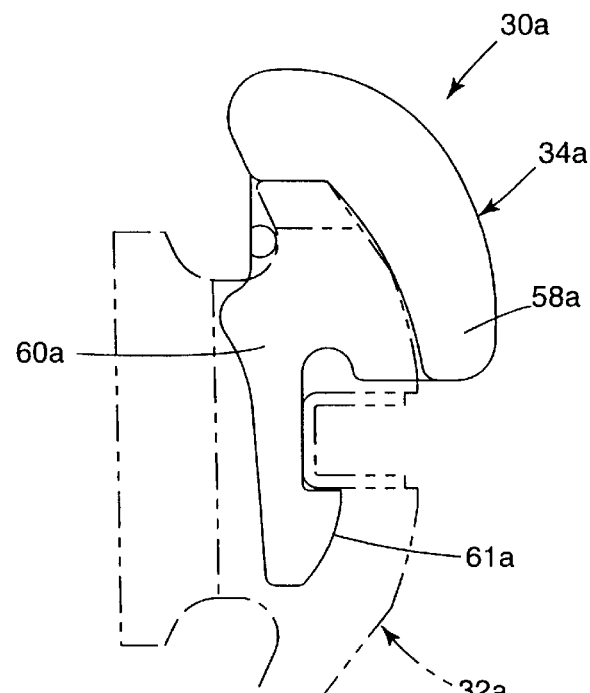
FIG. 6 is a side cross-sectional view of the assembly shown in FIG. 5 and taken along lines 6—6 of FIG. 5.

An orthodontic bracket assembly 30a according to another embodiment of the invention is illustrated in FIGS. 5 and 6. The assembly 30a includes a bracket 32a which is identical to the bracket 32 described above. The assembly 30a also includes a cap 34a that is essentially the same as the cap 34, except for the differences as noted below.

In particular, the cap 34a as shown in FIGS. 5 and 6 includes a second section 60a that is received in a channel 52a of the bracket 32a. In this instance, however, the second section 60a is constructed to be received in snap-fit relation along portions of a lingual wall and a gingival wall of an archwire slot liner 50a. During installation of the cap 34a on the bracket 32a, an outer curved camming surface 61a of the second section 60a contacts an occlusal-lingual corner of the archwire slot liner 50a and deflects the second section 60a in a lingual direction as the second section 60a moves in a gingival direction in the channel 52a. Once the cap 34a is fully seated on the bracket 32a and the camming surface 61a is located gingivally of the archwire slot liner 50a, the second section 60a self-deflects in a labial direction and comes to rest in the position shown in FIG. 6 where it hooks onto a gingival side of the archwire slot liner 50a.

The second section 60a is made of a metallic or polymeric material. Optionally, the second section 60a is made of a polymeric material that is either integrally molded, adhesively joined or otherwise coupled to a first section 58a. The first section 58a is optionally the same as the first section 58 as described above in connection with the assembly 30, except that a reinforcing framework may be omitted if desired.

Figure 7:
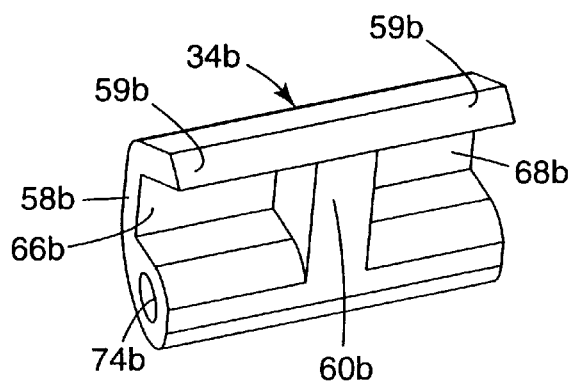
FIG. 7 is a perspective view of an orthodontic cap alone according to another embodiment of the invention.
Figure 8:
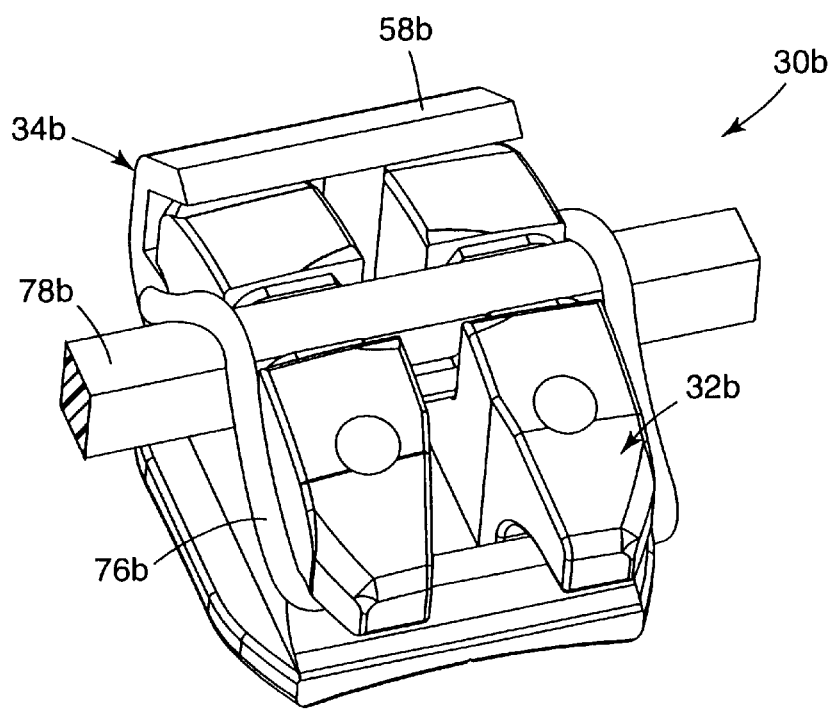
FIG. 8 is a reduced perspective view of the cap illustrated in FIG. 7 along with a bracket and a ligature.

An orthodontic bracket assembly 30b according to another embodiment of the invention is illustrated in FIG. 8, and includes an orthodontic bracket 32b as well as a cap 34b. The cap 34b is shown alone in FIG. 7.

The cap 34b includes a first section 58b and a second section 60b. The first section 58b includes a pair of concave portions 66b, 68b that are adapted to receive occlusal tips of a mesial-occlusal tiewing and a distal-occlusal tiewing of the bracket 32b respectively. The first section 58b includes wall portions 59b that extend over occlusal tips of the mesial-occlusal tiewing and the distal-occlusal tiewing in order to provide a barrier that prevents contact of such tiewings with the enamel of opposing teeth.

The cap 34b also includes a passageway 74b for receiving a ligature such as a wire ligature tie. Preferably, the passageway 74*b* is enclosed and the ligature is inserted in the passageway 74*b* by the manufacturer. Optionally, a structure such as a crimp or stop is provided to retain the ligature in place in the passageway 74*b*, at least until such time as the cap 34*b* has been assembled to the bracket 32*b*.

A wire ligature 76*b* is shown in FIG. 8. As illustrated, the ligature 76*b* serves to not only retain the cap 34*b* in place on the bracket 32*b*, but also to retain an archwire 78*b* in an archwire slot of the bracket 32*b*. As an alternative to a metallic wire, the ligature 76*b* may instead be made of an elastomeric material if desired.

The second section 60*b* of the cap 34*b* extends between the concave portions 66*b*, 68*b*, and is received in an occlusal-gingival channel of the bracket 32*b* when the cap 34*b* is assembled in the bracket 32*b*. The second section 60*b* serves to hinder unintentional movement of the cap 34*b* relative to the underlying bracket 32*b*. Optionally, the cap 34*b* may include mesial and distal portions (not shown, but somewhat similar to the mesial and distal portions 62, 64 respectively) that extend along mesial and distal sides of the mesial-occlusal tiewing and the distal-occlusal tiewing respectively of the bracket 32*b*, in order to further hinder unintentional movement of the cap 34*b* relative to the bracket 32*b*.

Preferably, the cap 34*b* is made of a material that is softer than the material of the bracket 32*b* when the bracket 32*b* is made of a metallic or ceramic material. Presently preferred materials include the stain-resistant elastomers and fluoropolymers described above. Alternatively, if the bracket 32*b* is made of a polymeric material, the cap 34*b* could be made of a somewhat harder material in order to prevent undue wear on the underlying bracket 32*b*.

Figure 9:
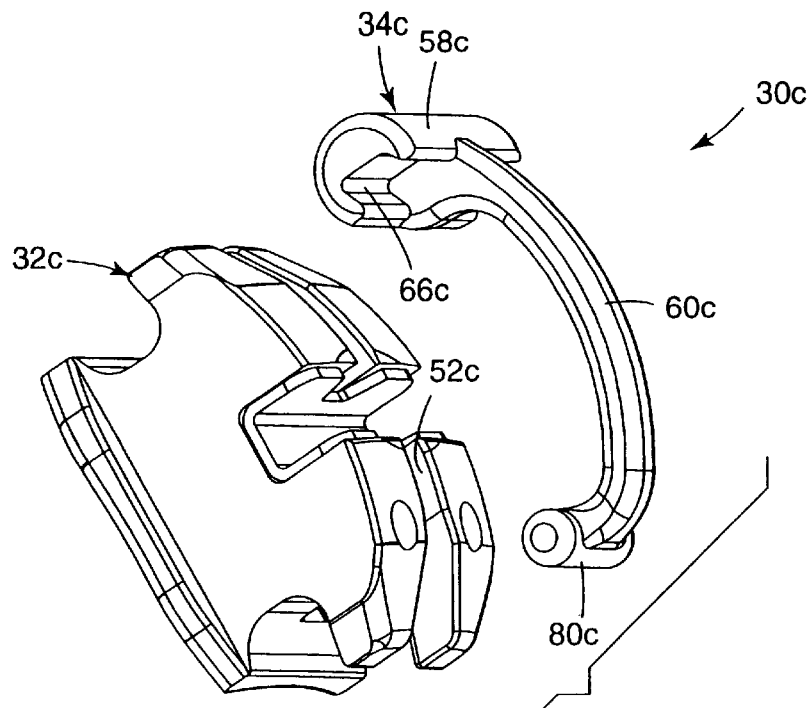
FIG. 9 is a perspective, exploded view of an orthodontic bracket and cap assembly constructed according to yet another embodiment of the invention.
Figure 10:
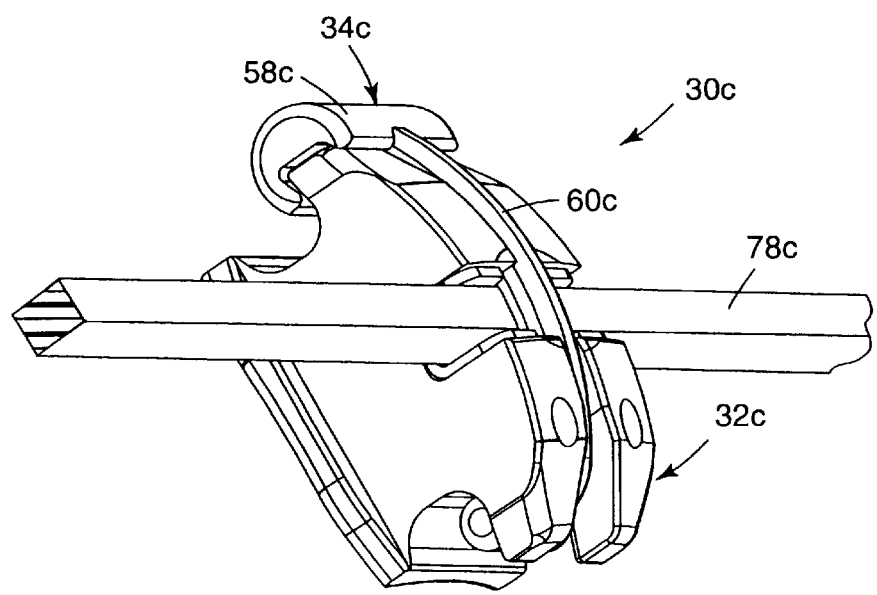
FIG. 10 is a view somewhat similar to FIG. 9 except that the bracket and cap are shown as they appear when assembled.

An orthodontic bracket assembly 30*c* according to another embodiment of the invention is illustrated in FIGS. 9 and 10. The assembly 30*c* includes an orthodontic bracket 32*c* that is similar to the bracket 32 described above, as well as a cap 34*c* that is releasably received on the bracket 32*c*.

The cap 34*c* includes a first section 58*c* and a second section 60*c*. The first section 58*c* includes a concave portion 66*c* for receiving an occlusal tip of a mesial-occlusal tiewing of the bracket 32*c*. Although not shown, the first section 58*c* also includes a second concave portion that receives an occlusal tip of the distal-occlusal tiewing of the bracket 32*c*. Optionally, both of the concave portions could be part of a single groove, if desired, or alternatively spaced apart by an inner rib that optionally forms part of the second section 60*c*.

The second section 60*c* extends in a generally occlusal-gingival direction along the length of a channel 52*c* of the bracket 32*c*. An outer, gingival end of the second section 60*c* includes a transverse bar 80*c* that extends in a generally mesial-distal direction. When the cap 34*c* is assembled to the bracket 32*c* as shown in FIG. 10, the bar 80*c* is received in notches or undercuts that are located lingually of gingival tips of the mesial-gingival tiewing and the distal-gingival tiewing of the bracket 32*c*.

A portion of the second section 60*c* is received in the channel 52*c*, and thus serves to substantially prevent lateral movement of the cap 34*c* relative to the bracket 32*c*. To assemble the cap 34*c* to the bracket 32*c*, the concave portions (including the concave portion 66*c*) are placed over the occlusal tips of the mesial-occlusal tiewing and the distal-occlusal tiewing. Next, the bar 80*c* is moved in a lingual direction across the gingival tips of the mesial-gingival tiewing and the distal-gingival tiewing, and then is released to snap in place lingually of such tips as shown in FIG. 10.

Preferably, the cap 34*c* is integrally molded of an aesthetically pleasing, stain resistant fluoropolymer or elastomer such as one of the materials described above. Consequently, the cap 34*c* has sufficient inherent resilience to permit assembly to the bracket 32*c* in snap-fit relation in the manner described above, and yet does not unintentionally detach from the bracket 32*c* during the course of treatment.

As illustrated in FIG. 10, the second section 60*c* of the cap 34*c* extends over a labial side of an archwire 78*c* received in an archwire slot of the bracket 32*c*. The second section 60*c* thereby functions to ligate the archwire 78*c* to the bracket 32*c* without the use of a separate ligature. If desired, the cap 34*c* can be detached from the bracket 32*c* and the archwire 78*c* can be ligated in conventional fashion using, for example, an elastomeric O-ring or a metal ligature tie such as are commonly available in the marketplace.

Figure 11:
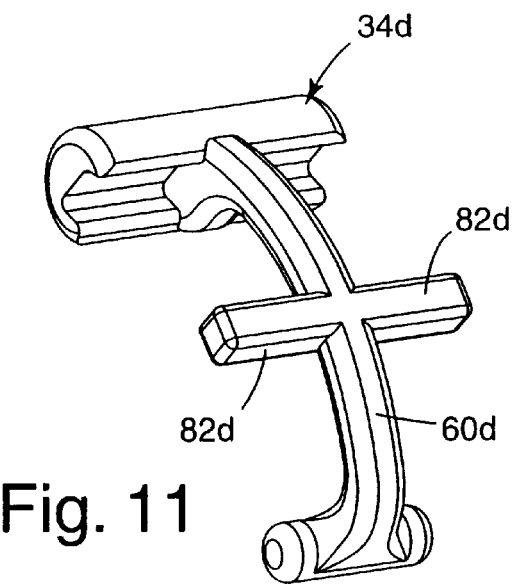
FIG. 11 is a perspective view of an orthodontic cap according to still another embodiment of the invention.

An orthodontic assembly according to another embodiment of the invention is identical to the assembly 30*c*, except that it includes a cap 34*d* as shown in FIG. 11 instead of the cap 34*c* shown in FIGS. 9 and 10. The cap 34*d* is essentially the same as the cap 34*c*, except that the cap 34*d* includes a second section 60*d* having a pair of arms 82*d* that extend in a generally mesial-distal direction. When the cap 34*d* is assembled to the bracket, the arms 82*d* extend along a labial side of the archwire slot and directly across a labial side of an archwire that is received in the archwire slot. The arms 82*d* provide enhanced rotational control over movement of the underlying tooth.

Figure 12:
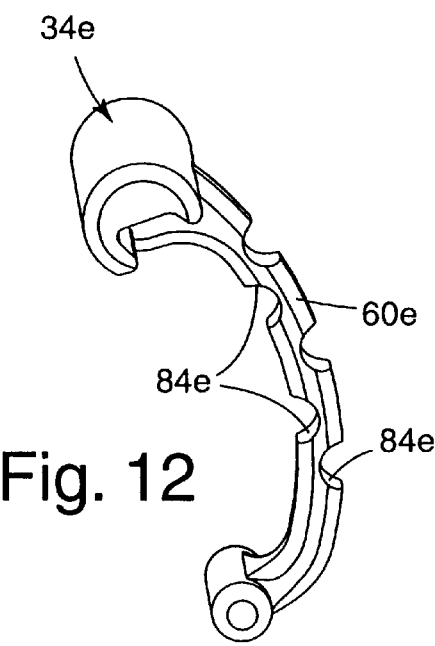
FIG. 12 is a perspective view of an orthodontic cap according to another embodiment of the invention.
Figure 13:
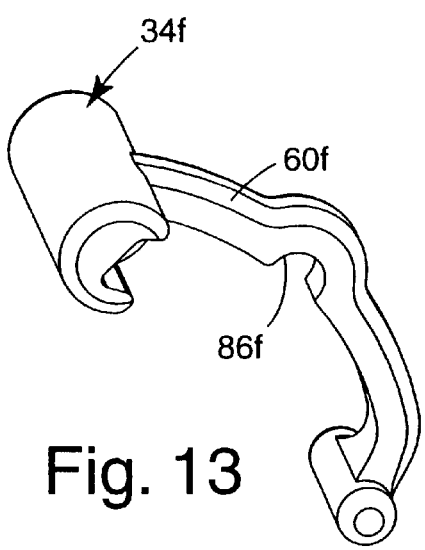
FIG. 13 is a perspective view of an orthodontic cap according to still another embodiment of the invention.

An orthodontic bracket assembly according to another embodiment of the invention is similar to the assembly 30*c*, but in this instance includes a cap 34*e* that is shown in FIG. 12. The cap 34*e* is essentially the same as the cap 34*c*, except that the cap 34*e* includes a number of notches 84*e* along the length of a second section 60*e*.

The notches 84*e* increase the flexibility of the second section 60*e*, so that deforming the second section 60*e* to allow the cap 34*e* to snap-fit onto the underlying bracket is somewhat easier. As such, the notches 84*e* enable the cap 34*e* to be made of a more rigid material, such as a rigid thermoplastic fluoropolymer. A suitable thermoplastic fluoropolymer is Halar. In all other respects, the cap 34*e* is the same as the cap 34*c* described above.

An orthodontic assembly constructed in accordance with yet another embodiment of the invention is identical to the orthodontic assembly 30*c* described above, except that a cap 34*f* is used in place of the cap 34*c*. The cap 34*f* has a second section 60*f* with a central bend that presents a U-shaped opening 86*f*. When the cap 34*f* is assembled to the bracket, the opening 86*f* lies over the archwire slot and provides additional clearance for an archwire received in the archwire slot. This additional clearance reduces binding and/or frictional forces between the bracket and the archwire that may otherwise retard movement of the associated tooth.

The opening 86*f* presents a clearance that enables the archwire to slide in the archwire slot without contact with the second section 60*f*. As a result, the cap 34*f* presents less frictional resistance to sliding movement of the archwire relative to the archwire slot of the bracket.

Figure 14:
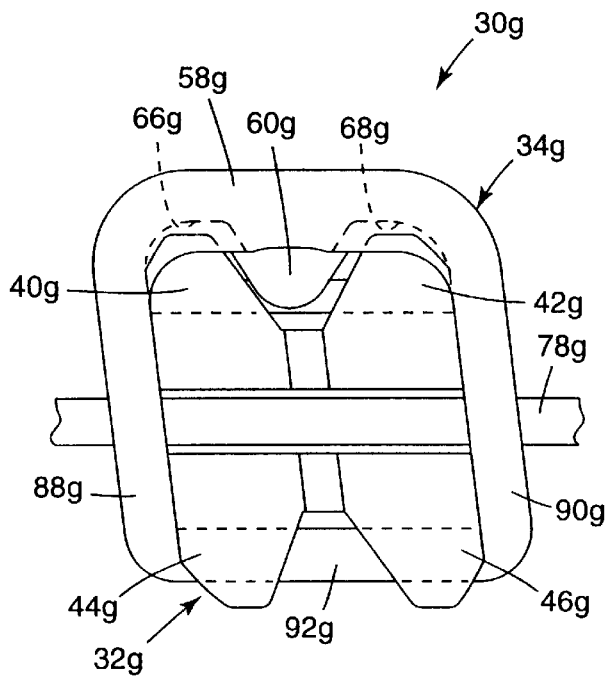
FIG. 14 is a front elevational view looking in a lingual direction of an orthodontic bracket and cap assembly constructed in accordance with yet another embodiment of the invention.
Figure 15:
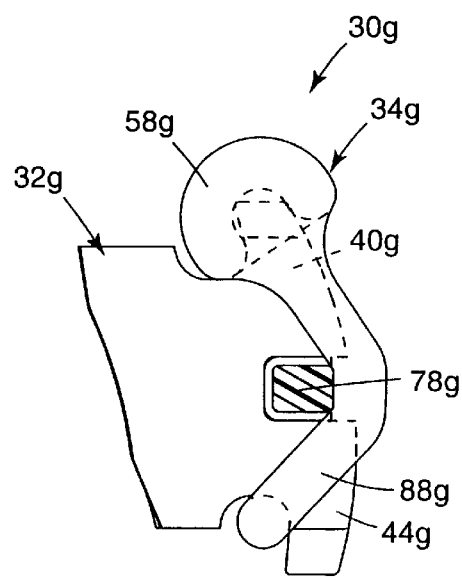
FIG. 15 is an end elevational view looking in a mesial-distal direction of the orthodontic bracket and cap assembly depicted in FIG. 14.

An orthodontic assembly 30*g* according to another embodiment of the invention is illustrated in FIGS. 14 and 15. The assembly 30*g* includes a bracket 32*g* that is similar to the bracket 32 described above. The assembly 30*g* also includes a cap 34*g* that is releasably connected to the bracket 32*g*.

The cap 34*g* includes a first section 58*g* having a pair of concave portions 66*g*, 68*g*. The concave 66*g* is received over an occlusal tip of a mesial-occlusal tiewing 40g of the bracket 32g, and the concave portion 68g is received over an occlusal tip of a distal-occlusal tiewing 42g of the bracket 32g. The first section 58g has a somewhat U-shaped configuration when viewed in cross-section in a mesial or distal direction, as shown in FIG. 17.

The cap 34g also includes a second section 60g which, in this embodiment, is in the nature of a depending protrusion that also spaces the concave portion 66g from the concave portion 68g. When the cap 34g is received on the bracket 32g, the second section 60g is received in an occlusal-gingival channel that is located between the tiewings 40g, 42g.

The cap 34g of this embodiment has an overall, generally annular shape with a mesial section 88g, a distal section 90g and a gingival section 92g. The mesial section 88g extends along a mesial side of the mesial-occlusal tiewing 40g as well as a mesial-gingival tiewing 44g, and the distal section 90g extends along a distal side of the distal-occlusal tiewing 42g as well as a distal-gingival tiewing 46g. The mesial section 88g and the distal section 90g also cross over a labial side of an archwire 78g in order to retain the archwire 78g and an archwire slot of the bracket 32g. The gingival section 92g extends along a lingual side of gingival tips of the mesial-gingival tiewing 44g and the distal-gingival tiewing 46g.

Figure 16:
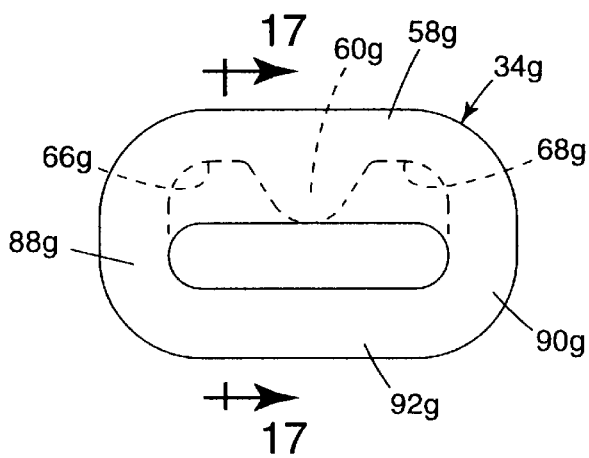
FIG. 16 is a front elevational view looking in a lingual direction of the cap alone that is shown in FIGS. 14 and 15, and illustrating the cap as it appears in its relaxed state before mounting on the bracket.
Figure 17:
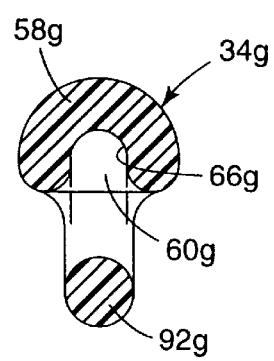
FIG. 17 is a side cross-sectional view of the cap shown in FIG. 16 and taken along the lines 17—17 of FIG. 16.

FIGS. 16 and 17 are illustrations of the cap 34g as it appears before assembly to the bracket 32g. As shown, the first section 58g has substantially the same configuration as appears in FIGS. 14 and 15 while the sections 88g, 90g, 92g are somewhat smaller than they appear after installation on the bracket 32g, since the thicker cross-sectional shape of the first section 58g will elongate less than the relatively thin cross-sectional shape of the sections 88g, 90g, 92g. Such construction will also ease installation of the cap 34g on the bracket 32g, since the sections 88g, 90g, 92g can be stretched to extend around the archwire 78g and behind the gingival tips of the tiewings 44g, 46g as needed while the first section 58g remains stable and in place.

The concave portions 66g, 68g, in combination with the second section 60g, serve to substantially prevent rotation of the cap 34g relative to the bracket 32g. As a result, the cap 34g will tend to remain in place and in the position shown in FIGS. 14 and 15 during the course of treatment. Preferably, the cap 34g is made of a stain resistant elastomeric material such as the materials described in U.S. Pat. Nos. 5,317,074 and 5,461,133.

FIGS. 18 and 19 illustrate an orthodontic assembly 30h according to another embodiment of the invention. The assembly 30h includes a bracket 32h and a cap 34h that is releasably coupled to the bracket 32h.

The bracket 32h is essentially the same as the bracket 32g, except that the bracket 32h is somewhat narrower in a mesial-distal direction as might be useful for installation on the patient's relatively narrow lower anterior teeth. The cap 34h is essentially the same as the cap 34g, except that the cap 34h has a somewhat narrower protruding second section 60h to fit within the confines of an occlusal-gingival channel 52h. The channel 52h does not include a V-shaped occlusal entry (as does the channel bracket 32g) and thus the second section 60h is somewhat narrower in order to fit within the channel 52h during installation.

FIG. 19 is an illustration of the cap 34h alone as it appears in its relaxed state and before assembly to the bracket 32h. Like the cap 34g, the cap 34h includes a first section 58h with a pair of concave portions 66h, 68h for receiving occlusal tips of occlusal bracket tiewings.

An orthodontic bracket assembly 30i according another embodiment of the invention is illustrated in FIG. 20, and includes a bracket 32i along with a cap 34i that is releasably connected to the bracket 32i. In this instance, the bracket 32i is the same as the bracket 32h shown in FIG. 18.

Additionally, the cap 34i is identical to the cap 34h, except that the cap 34i includes a gingival section 92i having an integrally molded projection 94i that extends in an occlusal-gingival direction. The projection 94i is received within a gingival, V-shaped entrance of a channel 52i of the bracket 32i. The projection 94i provides additional structure to prevent rotational movement of the cap 34i relative to the bracket 32i, and represents part of a second section (the other part of which is designated by the numeral 60i in FIGS. 20–22) in order to retain the cap 34i fixed in place on the bracket 32i as shown in FIG. 20.

FIGS. 21 and 22 are illustrations of the cap 34i alone, and as it appears before installation on the bracket 32i. Again, and as shown in FIGS. 21 and 22, the thicker sections of the cap 34i are molded to near net shape to provide less elongation than remaining sections of the cap 34i, so that installation of the cap 34i on the bracket 32i is facilitated.

A variety of modifications and additions to the embodiments described above will be apparent to those skilled in the art. For example, the configuration of the cap may be altered as necessary to best fit a particular bracket and retain the cap in place. Accordingly, the invention should not be deemed limited to the specific embodiments that are described in detail above, but instead only by a fair scope of the claims that follow along with their equivalents.

What is claimed is:

1. An orthodontic bracket assembly comprising:

an orthodontic bracket having a mesial-occlusal tiewing, a distal-occlusal tiewing, a mesial-gingival tiewing and a distal-gingival tiewing, the bracket including an archwire slot extending in a generally mesial-distal direction between the mesial-occlusal tiewing and the mesial-gingival tiewing and between the distal-occlusal tiewing and the distal-gingival tiewing, wherein the mesial-occlusal tiewing and the distal-occlusal tiewing each have an outermost, occlusal end, the bracket also having a channel extending in a generally occlusal-gingival direction between at least part of the mesial-occlusal tiewing and the distal-occlusal tiewing; and a cap releasably connected to the bracket, the cap including a first section in contact with the occlusal end of the mesial-occlusal tiewing and the occlusal end of the distal-occlusal tiewing and a second section extending at least partially along the channel.

2. An orthodontic bracket assembly according to claim 1 wherein the first section covers substantially all of the occlusal tiewing tips.

3. An orthodontic bracket assembly according to claim 1 wherein the cap is made of an elastomeric material.

4. An orthodontic bracket assembly according to claim 1 wherein the cap is made of a stain resistant polymer.

5. An orthodontic bracket assembly according to claim 4 wherein the polymer is a fluoropolymer.

6. An orthodontic bracket assembly according to claim 1 wherein the cap is made at least in part with a metallic material.

7. An orthodontic bracket assembly according to claim 6 wherein the metallic material is covered with a coating that resembles the color of natural teeth.

8. An orthodontic bracket assembly according to claim 1 wherein the first section includes at least one concave portion for receiving at least one occlusal tiewing tip.

9. An orthodontic bracket assembly according to claim 1 wherein the first section includes a pair of concave portions each receiving a respective one of the occlusal tiewing tips.

10. An orthodontic bracket assembly according to claim 1 wherein the first section includes a metallic substrate and a polymeric material fixed to the metallic substrate.

11. An orthodontic bracket assembly according to claim 1 wherein the occlusal tip of the mesial-occlusal tiewing includes a mesial side and the occlusal tip of the distal-occlusal tiewing includes a distal side, and wherein the first section includes a mesial portion and a distal portion that extend partially along the mesial side and the distal side respectively.

12. An orthodontic bracket assembly according to claim 1 wherein the second section includes an arm extending in a generally mesial-distal direction across the archwire slot.

13. An orthodontic bracket assembly according to claim 1 wherein the channel extends between at least part of the mesial-gingival tiewing and the distal-gingival tiewing.

14. An orthodontic bracket assembly according to claim 13 wherein the second section extends across the archwire slot in buccolabial relationship thereto in order to ligate an archwire in the archwire slot.

15. An orthodontic bracket assembly according to claim 14 wherein the second section includes at least one notch for facilitating snap-fit attachment of the cap to the bracket.

16. An orthodontic bracket assembly according to claim 14 wherein the second section includes an arm extending in a generally mesial-distal direction across the archwire slot in buccolabial relationship thereto in order to facilitate rotational control of the tooth.

17. An orthodontic bracket assembly according to claim 14 wherein the mesial-gingival tiewing and the distal-gingival tiewing each include an outermost gingival tip, and wherein the cap includes a gingival section that extends along the gingival tips.

18. An orthodontic bracket assembly according to claim 17 wherein the gingival section of the cap extends along the gingival tips in lingual relationship thereto.

19. An orthodontic bracket assembly comprising:
an orthodontic bracket having a mesial-occlusal tiewing, a distal-occlusal tiewing, a mesial-gingival tiewing and a distal-gingival tiewing, the bracket including an archwire slot extending in a generally mesial-distal direction between the mesial-occlusal tiewing and the mesial-gingival tiewing and between the distal-occlusal tiewing and the distal-gingival tiewing, wherein the mesial-occlusal tiewing and the distal-occlusal tiewing each have an outermost, occlusal tip, the bracket also having a channel extending in a generally occlusal-gingival direction between at least part of the mesial-occlusal tiewing and the distal-occlusal tiewing; and
a cap releasably connected to the bracket, the cap including a first section extending over the occlusal tiewing tips in occlusal relation thereto and a second section extending at least partially along the channel,
wherein the archwire slot includes a metallic liner with an occlusal side, a lingual side and a gingival side, wherein the channel extends lingually of the archwire slot, and wherein the second section of the cap extends at least partially along the gingival side of the archwire slot liner in snap-fit relation.

20. An orthodontic bracket assembly comprising:
an orthodontic bracket having a mesial-occlusal tiewing, a distal-occlusal tiewing, a mesial-gingival tiewing and a distal-gingival tiewing, the bracket including an archwire slot extending in a generally mesial-distal direction between the mesial-occlusal tiewing and the mesial-gingival tiewing and between the distal-occlusal tiewing and the distal-gingival tiewing, wherein the mesial-occlusal tiewing and the distal-occlusal tiewing each have an outermost, occlusal tip, the bracket also having a channel extending in a generally occlusal-gingival direction between at least part of the mesial-occlusal tiewing and the distal-occlusal tiewing; and
a cap releasably connected to the bracket, the cap including a first section extending over the occlusal tiewing tips in occlusal relation thereto and a second section extending at least partially along the channel,
wherein the archwire slot includes a metallic liner with an occlusal side, a lingual side and a gingival side, wherein the channel extends lingually of the archwire slot, and wherein the second section of the cap is bendable past its yield point to extend at least partially along the gingival side of the archwire slot liner.

21. An orthodontic bracket assembly comprising:
an orthodontic bracket having a mesial-occlusal tiewing, a distal-occlusal tiewing, a mesial-gingival tiewing and a distal-gingival tiewing, the bracket including an archwire slot extending in a generally mesial-distal direction between the mesial-occlusal tiewing and the mesial-gingival tiewing and between the distal-occlusal tiewing and the distal-gingival tiewing, wherein the mesial-occlusal tiewing and the distal-occlusal tiewing each have an outermost, occlusal tip, the bracket also having a channel extending in a generally occlusal-gingival direction between at least part of the mesial-occlusal tiewing and the distal-occlusal tiewing; and
a cap releasably connected to the bracket, the cap including a first section extending over the occlusal tiewing tips in occlusal relation thereto and a second section extending at least partially along the channel,
wherein the cap has a passageway for receiving a ligature.

22. An orthodontic bracket assembly according to claim 21 wherein the passageway is enclosed.

23. An orthodontic bracket assembly according to claim 22 and including a wire ligature received in the passageway.

24. An orthodontic bracket assembly comprising:
an orthodontic bracket having a mesial-occlusal tiewing, a distal-occlusal tiewing, a mesial-gingival tiewing and a distal-gingival tiewing, the bracket including an archwire slot extending in a generally mesial-distal direction between the mesial-occlusal tiewing and the mesial-gingival tiewing and between the distal-occlusal tiewing and the distal-gingival tiewing, wherein the mesial-occlusal tiewing and the distal-occlusal tiewing each have an outermost, occlusal tip, the bracket also having a channel extending in a generally occlusal-gingival direction between at least part of the mesial-occlusal tiewing and the distal-occlusal tiewing; and
a cap releasably connected to the bracket, the cap including a first section extending over the occlusal tiewing tips in occlusal relation thereto and a second section extending at least partially along the channel,
wherein the mesial-occlusal tiewing has a mesial side, wherein the distal-occlusal tiewing has a distal side and wherein the cap has an overall, generally annular shape with a mesial section that extends along the mesial side and a distal section that extends along the distal side, the mesial section and the distal section extending past the archwire slot in buccolabial relationship thereto for ligating an archwire in the archwire slot, the cap also including a gingival section interconnecting the mesial section and the distal section.

25. An orthodontic bracket assembly according to claim 24 wherein the channel extends between at least part of the mesial-gingival tiewing and the distal-gingival tiewing, and wherein the gingival section includes a protrusion received in the channel.

26. An orthodontic bracket assembly according to claim 24 wherein the mesial-gingival tiewing and the distal-gingival tiewing each include an outermost gingival tip, and wherein the gingival section of the cap extends along each gingival tip in lingual relationship thereto.

27. An orthodontic bracket assembly according to claim 24 wherein the cap is made up of an elastomeric material.

28. An orthodontic bracket assembly according to claim 27 wherein the cap is made of a stain-resistant elastomeric material.

29. An orthodontic bracket assembly comprising:
   an orthodontic bracket having a mesial-occlusal tiewing, a distal-occlusal tiewing and at least one gingival tiewing, the mesial-occlusal tiewing and the distal-occlusal tiewing each including an outermost occlusal tip, the bracket including an archwire slot extending in a generally mesial-distal direction, the bracket also having a channel extending in a generally occlusal-gingival direction between at least part of the mesial-occlusal tiewing and the distal-occlusal tiewing; and
   a cap releasably connected to the bracket, the cap including a first section extending over the occlusal tips in occlusal relation thereto and a second section extending at least partially along the channel, wherein the second section extends away from the first section in a generally gingival direction for insertion in the channel in a generally gingival direction.

30. An orthodontic bracket assembly according to claim 29 wherein the first section includes at least one concave portion for receiving at least one occlusal tiewing tip.

31. An orthodontic bracket assembly according to claim 29 wherein the first section includes a pair of concave portions each receiving a respective one of the occlusal tiewing tips.

32. An orthodontic bracket assembly according to claim 29 wherein the first section includes a metallic substrate and a polymeric material fixed to the metallic substrate.

33. An orthodontic bracket assembly according to claim 29 wherein the occlusal tip of the mesial-occlusal tiewing includes a mesial side and the occlusal tip of the distal-occlusal tiewing includes a distal side, and wherein the first section includes a mesial portion and a distal portion that extend partially along the mesial side and the distal side respectively.

34. An orthodontic bracket assembly according to claim 29 wherein the second section includes an arm extending in a generally mesial-distal direction across the archwire slot.

35. An orthodontic bracket assembly according to claim 29 wherein the second section extends across the archwire slot in buccolabial relationship thereto in order to ligate an archwire in the archwire slot.

36. An orthodontic bracket assembly comprising:
   an orthodontic bracket having a mesial-occlusal tiewing, a distal-occlusal tiewing and at least one gingival tiewing, the mesial-occlusal tiewing and the distal-occlusal tiewing each including an outermost occlusal tip, the bracket including an archwire slot extending in a generally mesial-distal direction, the bracket also having a channel extending in a generally occlusal-gingival direction between at least part of the mesial-occlusal tiewing and the distal-occlusal tiewing; and
   a cap releasably connected to the bracket, the cap including a first section extending over the occlusal tips in occlusal relation thereto and a second section extending at least partially along the channel,
   wherein the cap has a passageway for receiving a ligature.

37. An orthodontic bracket assembly comprising:
   an orthodontic bracket having a mesial-occlusal tiewing, a distal-occlusal tiewing and at least one gingival tiewing, the mesial-occlusal tiewing and the distal-occlusal tiewing each including an outermost occlusal tip, the bracket including an archwire slot extending in a generally mesial-distal direction, the bracket also having a channel extending in a generally occlusal-gingival direction between at least part of the mesial-occlusal tiewing and the distal-occlusal tiewing; and
   a cap releasably connected to the bracket, the cap including a first section extending over the occlusal tips in occlusal relation thereto and a second section extending at least partially along the channel,
   wherein the mesial-occlusal tiewing has a mesial side, wherein the distal-occlusal tiewing has a distal side and wherein the cap has an overall, generally annular shape with a mesial section that extends along the mesial side and a distal section that extends along the distal side, the mesial section and the distal section extending past the archwire slot in buccolabial relationship thereto for ligating an archwire in the archwire slot, the cap also including a gingival section interconnecting the mesial section and the distal section.

38. An occlusal cap for an orthodontic bracket having a first section and a second section, the first section having at least one occlusal concave portion for covering at least one occlusal tiewing tip of the bracket, the second section having an elongated configuration and extending outwardly from the first section in a generally gingival direction for reception in a channel of the bracket.

39. An occlusal cap according to claim 38 wherein the second section is curved outwardly in a buccolabial direction.

40. An occlusal cap according to claim 38 wherein the second section includes an outermost transverse bar.

41. An occlusal cap according to claim 38 wherein the first section includes a pair of concave portions that are spaced apart from each other.

42. An occlusal cap according to claim 38 wherein the cap includes an enclosed passageway for receiving a ligature.

43. An occlusal cap according to claim 38 wherein the second section includes an arm for extending across an archwire slot of the bracket.

* * * * *